United States Patent [19]

Ebert et al.

[11] Patent Number: 5,849,322
[45] Date of Patent: Dec. 15, 1998

[54] COMPOSITIONS AND METHODS FOR BUCCAL DELIVERY OF PHARMACEUTICAL AGENTS

[75] Inventors: Charles D. Ebert; Sonia J. Heiber, both of Salt Lake City, Utah; Mark K. Gutniak, Hässelby, Sweden

[73] Assignee: Theratech, Inc., Salt Lake City, Utah

[21] Appl. No.: 546,994

[22] Filed: Oct. 23, 1995

[51] Int. Cl.$^6$ .................................................... A61F 13/02
[52] U.S. Cl. ........................... 424/435; 424/434; 514/953
[58] Field of Search .................... 424/434, 435; 514/953

[56] References Cited

U.S. PATENT DOCUMENTS

| | | |
|---|---|---|
| 5,118,666 | 6/1992 | Habener . |
| 5,120,712 | 6/1992 | Habener . |
| 5,346,701 | 9/1994 | Heiber et al. . |
| 5,614,492 | 3/1997 | Habener . |

FOREIGN PATENT DOCUMENTS

0 619 322 A2  2/1994  European Pat. Off. .

OTHER PUBLICATIONS

G.I. Bell, et al., Exxon Duplication and Divergence in the Human Preproglucagon Gene, 304 Nature 368–371 (1983).

M. Gutniak, et al., Antidiabetogenic Effect of Glucagon–Like Peptide–1 (7–36) Amide in Normal Subjects and Patients with Diabetes Mellitus, The New England Journal of Medicine, 1316–1322 (1992).

M.A. Nauck, et al., Preserved Incretin Activity of Glucagon–like Peptide 1 [7–36 Amide] but Not of Synthetic Human Gastric Inhibitory Polypeptide in Patients with Type–2 Diabetes Mellitus, 91. The American Society for Clinical Investigation, Inc., 301–307 (1993).

M.A. Nauck, et al., Additive Insulinotropic Effects of Exogenous Synthetic Human Gastric Inhibitory Polypeptide and Glucagon–Like Peptied–1–7(7–36). Amide Infused at Near–Physiological Insulinotropic Hormone and Glucose Concentrations, 76 Journal of Clinical Endocrinology and Metabolism 912–917 (1993).

C. Ørskov, et al., Proglucagon Products in Plasma of Non–insulin–dependent Diabetics and Nondiabetic Controls in the Fasting State and after Oreal Glucose and Intravenous Arginine, 87 The American Society for Clinical Investigation, Inc., 415–423 (1991).

J.E. Gerich, Oral Hypoglycemic Agents, 321 New England Journal of Medicine 1231–1245.

M. Gutniak, et al., Glyburide Decreases Insulin Requirement, Increases –62 –cell Response to Mixed Meal, and Does Not Affect Insulin Sensitivity: Effects of Short–and Long–Term Combined Treatment in Secondary Failure to Sulfonylurea. 10 Diabetes Care 545–533 (1987).

H.E. Lebovitz and M.N. Feinglos, Sulfonylurea Drugs: Mechanism of Antidiabetic Action and Therapeutic Usefulness. 1 Diabetes Care 189–198 (1978).

(List continued on next page.)

*Primary Examiner*—Carlos Azpuru
*Attorney, Agent, or Firm*—Thorpe, North & Western, LLP

[57] ABSTRACT

A composition for transmucosally administering a drug to the oral cavity comprises an adhesive layer comprising a hydrophilic polymer having one surface adapted to contact a first tissue of the oral cavity and adhere thereto when wet and an opposing surface in contact with and adhering to an adjacent drug-containing layer comprising an effective amount of a drug and optionally an effective amount of a permeation enhancer, wherein the drug-containing layer is adapted to contact and be in drug transfer relationship with a mucosal tissue of the oral cavity when the adhesive layer contacts and adheres to the first tissue. Preferred drugs include peptides, such as glucagon-like insulinotropic peptides. A method of transmucosally administering a drug to the oral cavity is also disclosed.

44 Claims, 7 Drawing Sheets

OTHER PUBLICATIONS

C. Ørskov, et al., Biological Effects and Metabolic Rates of Glucagonlike Peptide–1 7–36, Amide and Glucagonlike Peptide–1 7–37 in Healthy Subjects Are Indistinguishavle, 42 Diabetes, 658–661 (1993).

D. Gefel, et al., Glucagon–Like Peptide–I Analogs: Effects on Insulin Secretion and Adenosine 3',5'–Monophosphate Formation, 126 Endocrinology, 2164–2168 (1990).

Some Aspects of Human Biochemistry, Chapter 25 (Hormones), pp. 735–741.

D.M. Nathan, et al., Insulinotropic Action of Glucagonlike Peptide–1–(7–37) in Diabetic and Nondiabetic Subjects, 15 Diabetes Care 270–276 (1992).

D. Harris and J. R. Robinson, Bioadhesive polymers in peptide drug delivery, Biomaterials 1990.

M.E. de Vries et al., Development in Buccal Drug Delivery, 8 Critical Reviews in Therapeutic Drug Carrier Systems, 271–303 (1991).

D. Harris and J.R. Robinson, Drug Delivery via the Mucous Membranes of the Oral Cavity, 81 Journal of Pharmaceutical Sciences 1–10 (1992).

M.E. de Vries, et al. Hydrogels for Buccal Drug Delivery: Properties Relevant for Muco–adhesion, 22 Journal of Biomedical Materials Research 1023–1032 (1988).

M.K. Gutniak, et al. Subcutaneous Injection of the Incretin Hormone Glucagon–Like Peptide 1 Abolishes Postprandial Glycemia in NIDDM, 17 Diabetes Care (1994).

M.A. Nauck et al., Normalization of Fasting Hyperglycaemia by Exogenous Glucagon–Like Peptide 1 (7–36 amide), in Type 2 (non–insulin dependent) Diabetic Patients, Diabetologia (1993).

Stephanie A. Amiel, Glucagon–Like Peptide: A Therapeutic Glimmer, 343 Lancet (Jan. 1 1994).

M.K. Gutniak et al., GLIP (Glucagon–Like Insulinotropic Peptide) Has A Stronger Antidiabetogenic Effect Than Gibenclamide, 36 Diabetologia (1993)(abstract).

I. Valverde et al., Glucagon–Like Peptide 1 (7–36) Amide: A Potent Glycongenic Hormone, 36 Diabetologia (1993)(abstract).

E. Delgado, et al. Identification and Characterization of GLP–1(7–36) Amide Receptors in Rat Skeletal Muscle, 36 Diabetologia (1993)(abstract).

M.L. Villanueva–Peñacarrillo et al., Presence and Characterization of GLP–1–(7–36) Amide Receptors in the Rat Liver, 36 Diabetologia (1993)(abstract).

H. Kofod, et al. Glucagon Acts on β–Cells By Cross Reaction With The GLP–1(7–36) Amide Receptor, 36 Diabetologia (1993)(abstract).

J.L. Gromada, et al. Induction of Glucose Responsiveness in Pancreatic β–Cells By Glucagon–Like Peptide 1. 36 Diabetologia (1993)(abstract).

S. Efendic, et al. Subcutaneous Injection of Glucagon–Like Insulinotropic Peptide Postprandial Glycemia in Type 2 Diabetes, 36 Diabetologia (1993)(abstract).

M.A. Nauck, et al., Insulinotropic Actions of GIP and GLP–1 (7–36 Amide), But Not of CCK–8 at Physiologically Elevated Amino Acid Concentrations, 36 Diabetologia (1993)(abstract).

E. Heinze, et al. Reduced GIP Contributes to Altered Insulin Response Following Oral Glucose in Women with Turner Syndrome, 36 Diabetologia (1993)(abstract).

COMPOSITIONS AND METHODS FOR BUCCAL DELIVERY OF PHARMACEUTICAL AGENTS

BACKGROUND OF THE INVENTION

This invention relates to compositions and methods for delivery of pharmaceutical agents into the body. More particularly, the invention relates to compositions and methods for delivery of drugs, especially peptide drugs, to a warm-blooded animal by transmucosal administration and particularly through the buccal tissue of the oral cavity.

Traditionally there has been very little work evaluating membranes of the oral cavity as sites of drug administration. Both the buccal and sublingual membranes offer advantages over other routes of administration. For example, drugs administered through the buccal and sublingual routes have a rapid onset of action, reach high levels in the blood, avoid the first-pass effect of hepatic metabolism, and avoid exposure of the drug to fluids of the gastrointestinal tract. Additional advantages include easy access to the membrane sites so that the drug can be applied, localized, and removed easily. Further, there is good potential for prolonged delivery through the buccal membrane. M. Rathbone & Jo Hadgraft, 74 *Int'l J. of Pharmaceutics* 9 (1991). Administration through the buccal mucosa may be better accepted than rectal dosing, for example, and generally avoids local toxic effects, such as has been a problem in nasal administration. B. Aungst & N. Rogers, 53 *Int'l J. Pharmaceutics* 227, 228 (1989).

The sublingual route has received far more attention than has the buccal route. The sublingual mucosa includes the membrane of the ventral surface of the tongue and the floor of the mouth, whereas the buccal mucosa constitutes the lining of the cheek and lips. The sublingual mucosa is relatively permeable, thus giving rapid absorption and acceptable bioavailabilities of many drugs. Further, the sublingual mucosa is convenient, easily accessible, and generally well accepted. This route has been investigated clinically for the delivery of a substantial number of drugs. It is the traditional route for administration of nitroglycerin and is also used for buprenorphine and nifedipine. D. Harris & J. Robinson, 81 *J. Pharmaceutical Sci.* 1 (1992).

The buccal mucosa is less permeable than the sublingual mucosa. The rapid absorption and high bioavailabilities seen with sublingual administration of drugs is not generally provided to the same extent by the buccal mucosa. D. Harris & J. Robinson, 81 *J. Pharmaceutical Sci.* 1, 2 (1992). The permeability of the oral mucosae is probably related to the physical characteristics of the tissues. The sublingual mucosa is thinner than the buccal mucosa, thus permeability is greater for the sublingual tissue. The palatal mucosa is intermediate in thickness, but is keratinized and thus less permeable, whereas the sublingual and buccal tissues are not keratinized.

The ability of molecules to permeate through the oral mucosae appears to be related to molecular size, lipid solubility, and ionization. Small molecules, e.g. less than about 300 daltons, appear to cross the mucosae rapidly. As molecular size increases, however, permeability decreases rapidly. Further, lipid-soluble compounds are more permeable through the mucosae than are non-lipid-soluble molecules. In this regard, the relative permeabilities of molecules seems to be related to their partition coefficients. The degree of ionization of molecules, which is dependent on the $pK_a$ of the molecule and the pH at the membrane surface, also greatly affects permeability of the molecules. Maximum absorption occurs when molecules are unionized or neutral in electrical charge; absorption decreases as the degree of ionization increases. Therefore, charged macromolecular drugs present the biggest challenge to absorption through the oral mucosae.

Substances that facilitate the transport of solutes across biological membranes, penetration enhancers, are well known in the art for administering drugs. V. Lee et al., 8 *Critical Reviews in Therapeutic Drug Carrier Systems* 91 (1991) [hereinafter "*Critical Reviews*"]. Penetration enhancers can be categorized as (a) chelators (e.g., EDTA, citric acid, salicylates), (b) surfactants (e.g., sodium dodecyl sulfate (SDS)), (c) non-surfactants (e.g., unsaturated cyclicureas), (d) bile salts (e.g., sodium deoxycholate, sodium taurocholate), and (e) fatty acids (e.g., oleic acid, acylcarnitines, mono- and diglycerides). The efficacy of enhancers in transporting both peptide and nonpeptide drugs across membranes seems to be positively correlated with the enhancer's hydrophobicity. *Critical Reviews* at 112. For example, the efficacy of bile salts in enhancing the absorption of insulin through nasal membranes is positively correlated with the hydrophobicity of the bile salts' steroid structure *Critical Reviews* at 115. Thus, the order of effectiveness is deoxycholate≦chenodeoxycholate≦cholate≦ursodeoxycholate. Conjugation of deoxycholate and cholate, but not fusidic acid derivatives, with glycine and taurine does not affect their enhancement potency. Transmucosal intestinal delivery of heparin is not apparent, as measured in terms of prolongation of partial thromboplastin time or release of plasma lipase activity, when administered through the colon of a baboon. However, significant activity is detected when the bile salts, sodium cholate or deoxycholate, are included in the formulation. *Critical Reviews* at 108.

Various mechanisms of action of penetration enhancers have been proposed. These mechanisms of action, at least for peptide and protein drugs, include (1) reducing the viscosity and/or elasticity of mucus layer, (2) facilitating transcellular transport by increasing the fluidity of the lipid bilayer of membranes, (3) facilitating paracellular transport by altering tight junctions across the epithelial cell layer, (4) overcoming enzymatic barriers, and (5) increasing the thermodynamic activity of the drugs. *Critical Reviews* at 117–125.

Many penetration enhancers have been tested and found effective in facilitating mucosal drug administration. Moreover, hardly any penetration enhanced products have reached the market place. Reasons for this include lack of a satisfactory safety profile respecting irritation, lowering of the barrier function, and impairment of the mucociliary clearance protective mechanism. *Critical Reviews* at 169–70. Further, for an enhancer to function adequately, the enhancer and drug combination is preferably held in position against mucosal tissues for a period of time sufficient to allow enhancer-assisted penetration of the drug across the mucosal membrane. In transdermal and transmucosal technology, this is often accomplished by means of a patch or other device that adheres to the skin layer by means of an adhesive.

Oral adhesives are well known in the art. See, for example, Tsuk et al., U.S. Pat. No. 3,972,995; Lowey, U.S. Pat. No. 4,259,314; Lowey, U.S. Pat. No. 4,680,323; Yukimatsu et al., U.S. Pat. No. 4,740,365; Kwiatek et al., U.S. Pat. No. 4,573,996; Suzuki et al., U.S. Pat. No. 4,292,299; Suzuki et al., U.S. Pat. No. 4,715,369; Mizobuchi et al., U.S. Pat. No. 4,876,092; Fankhauser et al., U.S. Pat. No. 4,855,142; Nagai et al., U.S. Pat. No. 4,250,163; Nagai et al., U.S.

Pat. No. 4,226,848; Browning, U.S. Pat. No. 4,948,580; Schiraldi et al., U.S. Reissue Patent Re.33,093; and J. Robinson, 18 *Proc. Intern. Symp. Control. Rel. Bioact. Mater.* 75 (1991). Typically, these adhesives consist of a matrix of a hydrophilic, e.g., water soluble or swellable, polymer or mixture of polymers that can adhere to a wet mucous surface. These adhesives may be formulated as ointments, thin films, tablets, troches, and other forms. Often, these adhesives have had medicaments mixed therewith to effectuate slow release or local delivery of a drug. Some, however, have been formulated to permit adsorption through the mucosa into the circulatory system of the individual. Interactions between adhesives and drugs, however, often impair release of the drug from the dosage form and permeation through the mucosa.

There is nothing in the art that is directed specifically with overcoming problems associated with enhancer-assisted buccal or sublingual delivery of drug molecules, particularly large drug molecules, wherein the drug molecule is subject to these adhesive/drug interactions and the ensuing reduced efficiency of delivery.

As an example, glucagon-like insulinotropic peptides, e.g. GLP-1(7–36)amide, are antidiabetogenic agents being investigated for treatment of diabetes mellitus that have heretofore been administered intravenously, subcutaneously, or by some other invasive route, and are too large for transdermal delivery. Diabetes mellitus afflicts nearly 15 million people in the United States. About 15 percent have insulin-dependent diabetes (IDDM; type 1 diabetes), which is believed to be caused by autoimmune destruction of pancreatic islet beta cells. In such patients, insulin therapy is essential for life. About 80% of patients have non-insulin-dependent diabetes (NIDDM; type 2 diabetes), a heterogeneous disorder characterized by both impaired insulin secretion and insulin resistance. A few patients who appear to have NIDDM may actually have a slowly progressive form of IDDM and eventually become dependent on insulin. Most patients with NIDDM, however, can be treated without insulin. They are usually overweight and have the insulin resistance of obesity superimposed on the insulin resistance intrinsic to the disease. Weight loss, especially early in the disease, can restore normal glucose levels in the blood of these patients. Their diabetes may develop when the impact of the combined insulin resistances exceeds the ability of their pancreatic beta cells to compensate. Plasma insulin levels in such patients, which are often higher than those in people of normal weight who do not have diabetes, are not appropriate to their obesity and hyperglycemia. People with NIDDM who are not obese may have a primary defect in insulin secretion in which elevations of plasma glucose levels cause not only insulin resistance but also the further deterioration of pancreatic beta cell functioning. J. E. Gerich, Oral Hypoglycemic Agents, 321 *N. Engl. J. Med.* 1231 (1989).

NIDDM patients are generally treated with diet modifications and sulfonylureas and/or diguanides. H. E. Lebovitz & M. N. Feinglos, Sulfonylurea Drugs: Mechanism of Antidiabetic Action and Therapeutic Usefulness, 1 *Diabetes Care* 189 (1978). Oral hypoglycemic agents account for about 1 percent of all prescriptions in the United States. JOE. Gerich, 321 *N. Engl. J. Med.* 1231 (1989) Unfortunately, about 11–36% of NIDDM patients fail to respond well to diet and sulfonylurea therapy after one year of treatment. Within 5–7 years, about half of NIDDM patients receiving sulfonylurea treatment need to start insulin therapy. These patients tend to be resistant to insulin, thus high doses of insulin are administered, which in turn leads to hyperinsulinemia which can play a role in the development of atherosclerosis. D. A. Robertson et al., Macrovascular Disease and Hyperinsulinaemia, in *Bailliere's Clinical Endocrinology and Metabolism* 407–24 (M. Nattras & P. J. Hale eds., 1988).

In warm-blooded animals and humans, glucagon-like insulinotropic peptides stimulate insulin release, lower glucagon secretion, inhibit gastric emptying, and enhance glucose utilization. M. K. Gutniak et al., Antidiabetogenic Effect of Glucagon-Like Peptide-1 (7–36)amide in Normal Subjects and Patients with Diabetes Mellitus, 326 *N. Engl. J. Med.* 1316 (1992); D. M. Nathan et al., Insulinotropic Action of Glucagonlike Peptide-1-(7(37) in Diabetic and Nondiabetic Subjects, 15 *Diabetes Care* 270 (1992); M. A. Nauck et al., Normalization of Fasting Hyperglycaemia by Exogenous Glucagon-Like Peptide 1 (7–36amide) in Type 2 (Non-Insulin-Dependent) Diabetic Patients, 36 *Diabetologia* 741 (1993). Further, these peptide drugs are inherently safe since the insulinotropic effects are strictly glucose dependent, thus limiting the risk of hypoglycemia in response to therapeutic use thereof. M. A. Nauck et al., Normalization of Fasting Hyperglycaemia by Exogenous Glucagon-like Peptide 1 (7–36 amide) in Type 2 (Non-Insulin-Dependent) Diabetic Patients, 36 *Diabetologia* 741 (1993). These properties make such peptides serious candidates for a therapeutic drug in treatment of non-insulin dependent diabetes mellitus (NIDDM).

GLP-1(7–36)amide is a gastrointestinal hormone processed from the preproglucagon gene. Preproglucagon is a polyprotein hormone precursor comprising a 20-amino acid signal peptide and a 160-amino acid prohormone, proglucagon (PG). PG has been shown to be processed differently in the pancreas and the small intestine of man. C. ørskov et al., Pancreatic and Intestinal Processing of Proglucagon in Man, 30 *Diabetologia* 874 (1987). In the pancreas, the main products are (a) glucagon (PG amino acids 33–61), (b) a glycentin-related pancreatic peptide (GRPP) (PG amino acids 1–30), and (c) a large peptide-designated major proglucagon fragment (MPGF) (PG amino acids 72–158) that contains two glucagon-like sequences The only proglucagon derived pancreatic peptide with known biological activity is glucagon. In the small intestine, the main products of proglucagon are (a) enteroglucagon (PG amino acids 1–69), which includes the glucagon sequence of amino acids, (b) GLP-1 (PG amino acids 78–107), and (c) GLP-2 (PG amino acids 126–158). C. ørskov et al., Proglucagon Products in Plasma of Noninsulin-dependent Diabetics and Nondiabetic Controls in the Fasting State and after Oral Glucose and Intravenous Arginine, 87 *J. Clin. Invest.* 415 (1991). GLP-1(7–36)amide is the naturally occurring form in humans, C. ørskov et al., Complete Sequences of Glucagon-like Peptide-1 from Human and Pig Small Intestine, 264 *J. Biol. Chem.* 12826 (1989), but a variant, termed GLP-1(7–37), has been shown to have indistinguishable biological effects and metabolic rates in healthy individuals, D. Gefel et al., Glucagon-Like Peptide-I Analogs: Effects on Insulin Secretion and Adenosine 3'5'-Monophosphate Formation, 126 *Endocrinology* 2164 (1990); C. ørskov et al., Biological Effects and Metabolic Rates of Glucagonlike Peptide-1 7–36 Amide and Glucagonlike Peptide-1 7–37 in Healthy Subjects Are Indistinguishable, 42 *Diabetes* 658 (1993). It has long been believed that an endocrine transmitter produced in the gastrointestinal tract, or incretin, stimulates insulin secretion in response to food intake. Since GLP-1(7–36) amide is released during a meal and after oral glucose administration and potentiates glucose-induced insulin release, this peptide may be an important incretin. J. M.

Conlon, Proglucagon-derived Peptides: Nomenclature, Biosynthetic Relationships and Physiological Roles, 31 *Diabetologia* 563 (1988); J. J. Holst et al., Truncated Glucagon-like Peptide 1, an Insulin-releasing Hormone from the Distal Gut, 211 *FEBS Lett.* 169 (1987); M. Gutniak et al., Antidiabetogenic Effect of Glucagon-like Peptide-1 (7–36)amide in Normal Subjects and Patients with Diabetes Mellitus, 326 *N. Engl. J. Med.* 1316 (1992).

An improved treatment regime for NIDDM patients exhibiting a secondary failure to sulfonylurea should give a satisfactory metabolic control without creating marked hyperinsulinemia. Until now, there have been no other serious candidates for a drug that can be used as such a treatment. Glucagon-like insulinotropic peptides, such as GLP-1(7–36)amide, appear to be the most promising treatment of diabetes. J. Eng, U.S. Pat. No. 5,424,286; S. E. Bjorn et al., WO 9517510; J. A. Galloway et al., EP 658568; H. Agerbk et al., WO 9505848; D. E. Danley et al., EP 619322; G. C. Andrews, WO 9325579; O. Kirk et al., WO 9318785; D. I. Buckley et al., WO 9111457; J. F. Habener, U.S. Pat. No. 5,118,666; J. F. Habener, WO9011296; J. F. Habener, WO 8706941; J. F. Habener, U.S. Pat. No. 5,120, 712. It has been found previously that the combination therapy of a glucagon-like insulinotropic peptide and a sulfonyl urea exerts a synergistic effect on glycemia and insulin release. S. Efendic et al., WO 9318786.

In view of the foregoing, it will be appreciated that compositions and methods for buccal delivery of certain drugs, such as peptide drugs and preferably insulinotropic peptides such as GLP-1(7–36)amide, wherein drug/adhesive interactions are greatly reduced would be significant advancements in the art.

OBJECTS AND SUMMARY OF THE INVENTION

It is an object of the present invention to provide a composition and method for delivery of a drug through an oral membrane wherein inhibition of transmembrane flux due to drug/adhesive interactions is greatly reduced.

It is also an object of the invention to provide a composition and method for delivery of a peptide drug through the buccal mucosa.

It is another object of the invention to provide a composition and method for delivery of a glucagon-like insulinotropic peptide through the buccal mucosa.

These and other objects are accomplished by providing a system for transmucosally administering a drug to the oral cavity comprising an adhesive layer comprising a hydrophilic polymer having one surface adapted to contact a first tissue of the oral cavity and adhere thereto when wet and an opposing surface in contact with and adhering to an adjacent drug-containing layer comprising an effective amount of a drug and optionally an effective amount of a permeation enhancer, the drug-containing layer adapted to contact and be in drug transfer relationship with a mucosal tissue of the oral cavity when the adhesive layer contacts and adheres to the first tissue. Preferred permeation enhancers include cell envelope disordering compounds, solvents, steroidal detergents, bile salts, chelators, surfactants, non-surfactants, fatty acids, and mixtures thereof, with bile salt enhancers being more preferred. The drug is preferably a peptide drug, such as insulinotropic peptides, calcitonin, insulin, desmopressin, parathyroid hormone, and amylin, and their precursors, analogues, and fragments, wherein such precursors, analogues, and fragments have pharmacological activity. The hydrophilic polymer preferably comprises at least one member selected from the group consisting of hydroxypropyl cellulose, hydroxypropyl methylcellulose, hydroxyethylcellulose, ethylcellulose, carboxymethyl cellulose, dextran, gaur-gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and mixtures thereof A mixture of polyethylene oxide and polyacrylic acid is especially preferred. The adhesive layer additionally can contain one or more members selected from the group consisting of fillers, tableting excipients, lubricants, flavors, dyes, and the like, and the drug-containing layer additionally can contain one or members selected from the group consisting of tableting excipients, fillers, flavors, taste-masking agents, dyes, stabilizers, enyzme inhibitors, lubricants, and the like. Preferably, the system is a bilayer tablet wherein the adhesive layer is in contact with and adheres to the gingiva and the drug-containing layer is in drug transfer relationship with the buccal mucosa.

A method for transmucosally administering a drug to an oral cavity comprises applying to a first tissue of the oral cavity a system comprising an adhesive layer comprising a hydrophilic polymer having one surface adapted to contact the first tissue of the oral cavity and adhere thereto when wet and an opposing surface in contact with and adhering to an adjacent drug-containing layer comprising an effective amount of a drug and optionally an effective amount of a permeation enhancer, the drug-containing layer adapted to contact and be in drug transfer relationship with a mucosal tissue of the oral cavity when the adhesive layer contacts and adheres to the first tissue.

DETAILED DESCRIPTION OF THE INVENTION

Before the present composition and method for buccal delivery of a drug are disclosed and described, it is to be understood that this invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a bilayer tablet containing "a drug" includes a mixture of two or more drugs, reference to "an adhesive" includes reference to one or more of such adhesives, and reference to "a bile salt" includes reference to a mixture of two or more bile salts.

In describing and claiming the present invention, the following terminology will be used in accordance with the definitions set out below.

As used herein, "glucagon-like insulinotropic peptides" means insulinotropic peptides that exhibit substantial amino acid sequence similarity to glucagon, such as GLP-1(7–36) amide and precursors, analogues, and fragments thereof wherein said precursors, analogues, and fragments have insulinotropic, or insulin stimulating, activity. Such precursors, analogues, and fragments include polypeptides having the primary sequence of GLP-1(7–36)amide wherein one or more L-amino acid residues are coupled to the C-terminus or N-terminus thereof; wherein the C-terminus contains a carboxyl group, an amide or substituted amide, an ester, or salt; and combinations thereof. Also included in the definition are peptides substantially homologous to GLP-1(7–36)amide and precursors, analogues, and fragments thereof, provided such homologous peptides also contain insulinotropic activity. As used herein, "substantially homologous" refers to peptides that retain functionality despite differences in primary structure from peptides to which they are compared. For example, a peptide substantially homologous to GLP-1(7–36)amide is one that retains functionality as an insulinotropic agent although it may include additional amino acid residues or be a truncation, deletion variant, or substitution variant thereof. A substitution variant is one that contains a conservative substitution of one or more amino acid residues. A conservative substitution is a substitution of one amino acid residue for another wherein functionality of the peptide is retained, in this case, functionality as an insulinotropic agent. Amino acid residues belonging to certain conservative substitution groups can sometimes substitute for another amino acid residue in the same group. One such classification of conservative substitution groups is as follows: (a) Pro; (b) Ala, Gly; (c) Ser, Thr; (d) Asn, Gln; (e) Asp, Glu; (f) His; (g) Lys, Arg; (h) Cys; (i) Ile, Leu, Met, Val; and (j) Phe, Trp, Tyr. M. Jimenez-Montano & L. Zamora-Cortina, Evolutionary model for the generation of amino acid sequences and its application to the study of mammal alpha-hemoglobin chains, Proc. VIIth Int'l Biophysics Congress, Mexico City (1981). Another such classification is described in M. Dayhoff et al., Atlas of Protein Sequence and Structure 1978 (Nat'l Biomed. Res. Found., Washington, D.C.), hereby incorporated by reference. Other variations that are to be considered substantially homologous include substitution of D-amino acids for the naturally occurring L-amino acids, substitution of amino acid derivatives such as those containing additional side chains, and substitution of non-standard amino acids, ire. α-amino acids that are rare or do not occur in proteins. The primary structure of a substantially homologous peptide is limited only by function.

As used herein, "peptide" means peptides of any length and includes proteins. The terms "polypeptide" and "oligopeptide" are used herein without any particular intended size limitation, unless a particular size is otherwise stated. Typical of peptides that can be utilized are those selected from group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein drug which may be utilized is one of functionality.

As used herein, "chemical enhancer," "penetration enhancer," "permeation enhancer," and the like shall be inclusive of all enhancers which increase the flux of a permeant, drug, or other molecule across the mucosa and is limited only by functionality. In other words, all cell envelope disordering compounds, solvents, steroidal detergents, bile salts, chelators, surfactants, non-surfactants, fatty acids, and any other chemical enhancement agents are intended to be included.

The flux of a drug or analyte across the mucosa can be increased by changing either the resistance (the diffusion coefficient) or the driving force (the gradient for diffusion). Flux may be enhanced by the use of so-called penetration or permeation or chemical enhancers.

Permeation enhancers are comprised of two primary categories of components, i.e., cell-envelope disordering compounds and solvents or binary systems containing both cell-envelope disordering compounds and solvents. As discussed above, other categories of permeation enhancer are known, however, such as steroidal detergents, bile salts, chelators, surfactants, non-surfactants, and fatty acids.

Cell envelope disordering compounds are known in the art as being useful in topical pharmaceutical preparations and function also in drug delivery through the skin or mucosa. These compounds are thought to assist in dermal penetration by disordering the lipid structure of the stratum corneum cell-envelopes. A list of such compounds is described in European Patent Application 43,738, published Jun. 13, 1982, which is incorporated herein by reference. It is believed that any cell envelope disordering compound is useful for purposes of this invention. Exemplary of the cell envelope disordering compounds are those represented by the formula:

R—X wherein R is a straight-chain alkyl of about 7 to 16 carbon atoms, a non-terminal alkenyl of about 7 to 22 carbon atoms, or a branched-chain alkyl of from about 13 to 22 carbon atoms, and X is —OH, —COOCH$_3$, —COOC$_2$H$_5$, —OCOCH$_3$, —SOCH$_3$, —P(CH$_3$)$_2$O, —COOC$_2$H$_4$OC$_2$H$_4$OH, —COOCH(CHOH)$_4$CH$_2$OH, —COOCH$_2$CHOHCH3, —COOCH$_2$CH(OR")CH$_2$OR", —(OCH$_2$CH$_2$)$_m$OH, —COOR', or —CONR'$_2$ where R' is —H, —CH$_3$, —C$_2$H$_5$, —C$_3$H$_7$ or —C$_2$H$_4$OH; R" is —H, or a non-terminal alkenyl of about 7 to 22 carbon atoms; and m is 2–6; provided that when R" is an alkenyl and X is —OH or —COOH, at least one double bond is in the cis-configuration.

Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones (azones) and the like.

U.S. Pat. No. 4,537,776, Cooper, issued Aug. 27, 1985, contains an excellent summary of prior art and background information detailing the use of certain binary systems for permeant enhancement. Because of the completeness of that disclosure, the information and terminology utilized therein are incorporated herein by reference.

Similarly, European Patent Application 43,738, referred to above, teaches using selected diols as solvents along with a broad category of cell-envelope disordering compounds for delivery of lipophilic pharmacologically-active compounds. Because of the detail in disclosing the cell-envelope disordering compounds and the diols, this disclosure of European Patent Application 43,738 is also incorporated herein by reference.

A binary system for enhancing metaclopramide penetration is disclosed in UK Patent Application GB 2,153,223 A, published Aug. 21, 1985, and consists of a monovalent alcohol ester of a C8–32 aliphatic monocarboxylic acid (unsaturated and/or branched if C18–32) or a C6–24 aliphatic monoalcohol (unsaturated and/or branched if C14–24) and an N-cyclic compound such as 2-pyrrolidone, N-methylpyrrolidone and the like.

Combinations of enhancers consisting of diethylene glycol monoethyl or monomethyl ether with propylene glycol monolaurate and methyl laurate are disclosed in U.S. Pat. No. 4,973,468 as enhancing the transdermal delivery of steroids such as progestogens and estrogens. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of $C_2$ to $C_4$ alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol and an inert diluent such as water.

Other permeation enhancers, not necessarily associated with binary systems include DMSO or aqueous solutions of DMSO such as taught in Herschler, U.S. Pat. No. 3,551,554; Herschler, U.S. Pat. No. 3,711,602; and Herschler, U.S. Pat. No. 3,711,606, and the azones (n-substituted-alkyl-azacycloalkyl-2-ones) such as noted in Cooper, U.S. Pat. No. 4,557,943.

As used herein, "bile salts" means the steroidal detergents that are the natural or synthetic salts of cholanic acid, e.g. the salts of cholic and deoxycholic acid or combinations of such salts, and the unionized acid form is also included. The salts of the conjugates of the bile acid with glycine or taurine are preferred, with the taurine salts being particularly preferred. Bile salt analogs having the same physical characteristics and that also function as permeation enhancers are also included in this definition. "NaTC" is the bile salt, sodium taurocholate. "CHAPS" is the bile salt analog, 3-[3-cholamidopropyl)dimethylammonio]-1-propane sulfate, inner salt.

As used herein, "transmucosal" or similar terms means passage of a permeant into and through the mucosa to achieve effective therapeutic blood levels or deep tissue levels of a drug.

As used herein, the term "permeant," "drug," or "pharmacologically active agent" or any other similar term means any chemical or biological material or compound, inclusive of peptides, suitable for transmucosal administration by the methods previously known in the art and/or by the methods taught in the present invention, that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may be systemic. This invention is not drawn to novel permeants or to new classes of active agents. Rather it is limited to the mode of delivery of agents or permeants which exist in the state of the art or which may later be established as active agents and which are suitable for delivery by the present invention. Such substances include broad classes of compounds normally delivered into the body, including through body surfaces and membranes, including skin. In general, this includes but is not limited to: antiinfectives such as antibiotics and antiviral agents; analgesics and analgesic combinations; anorexics; antihelminthics; antiarthritics; antiasthmatic agents; anticonvulsants; antidepressants; Antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; and tranquilizers. By the method of the present invention, both ionized and nonionized drugs may be delivered, as can drugs of either high or low molecular weight.

As used herein, "effective amount" means an amount of a drug or pharmacologicallly active agent that is nontoxic but sufficient to provide the desired local or systemic effect and performance at a reasonable benefit/risk ratio attnding any medical treatment. An effective amount of a permeation enhancer as used herein means an amount selected so as to provide the selected increase in mucosal permeability and, correspondingly, the desired depth of penetration, rate of administration and amount of drug delivered.

As used herein, "adhesive," "adhesive polymer", "mucoadhesive", or such similar terms refers to hydrophilic polymers, natural or synthetic, which, by the hydrophilic designation, can be either water soluble or swellable and which are compatible with the enhancers and drugs. Such adhesives function for adhering the bilayer tablet dosage form to the mucous tissues of the oral cavity, such as the gingiva. These adhesives do not adversely affect the activity of the drug. Such adhesives are inclusive of hydroxypropyl cellulose, hydroxypropyl methylcellulose, hydroxy ethylcellulose, ethylcellulose, carboxymethyl cellulose, dextran, gaur-gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and mixtures thereof, and the like.

Figure 1:
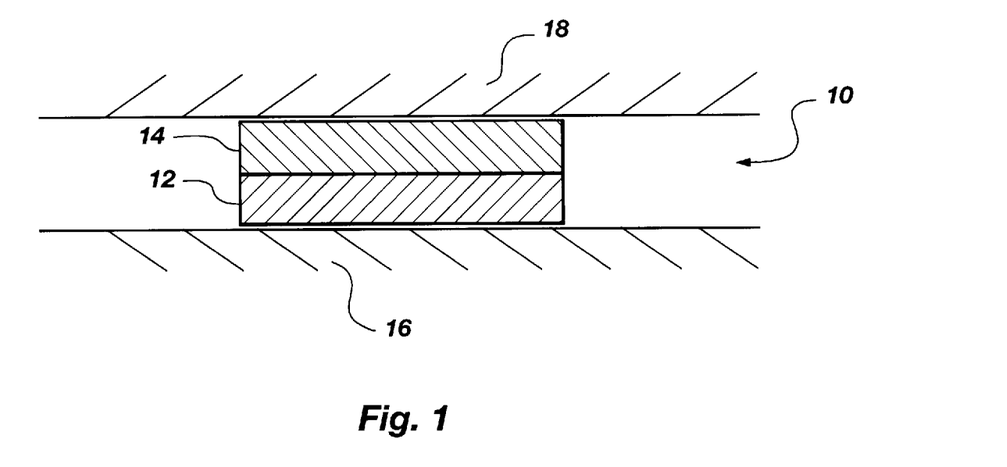
FIG. 1 shows a sectional view of a dosage form according to the present invention wherein a drug-containing layer thereof is in drug-transfer relationship with buccal mucosa.

Referring to FIG. 1 there is shown an illustrative dosage form according to the present invention for administering a drug, preferably a peptide drug, through an oral mucosal tissue such that drug/adhesive interactions that inhibit efficient transmembrane flux of the drug through the mucosal tissue are greatly diminished or eliminated. The dosage form is shown as a bilayer tablet 10 comprising an adhesive layer 12 and an active or drug-containing layer 14. The adhesive layer 12 is formulated to adhere to a mucous surface in the oral cavity such that the active layer 14 is in a drug-transfer relationship with a mucosal tissue such that the drug permeates through the mucosal tissue and is absorbed into the bloodstream of the individual. In the illustrative embodiment of FIG. 1, the tablet 10 is placed in the oral cavity such that the adhesive layer 12 adheres to a gingival surface 16 and the active layer 14 is in drug-transfer relationship with the buccal mucosa 18.

Bilayer tablets are made by classical bilayer tablet compression techniques on a suitable press. In reference to FIG. 1, the bilayer tablets 10 consist of an adhesive layer 12 and an active or drug-containing layer 14, which can be of a different color to distinguish the layers for purposes of application. The identification of the drug-containing, non-adhesive layer 14 facilitates application by the patient and prevents incidental adhesion of other oral tissues to the tablet. The adhesive layer 12 is prepared by either dry mixing the ingredients and compressing them into a tablet or by wet granulating the ingredient mixture and then compressing according to accepted pharmaceutical techniques. In general, it has been found suitable to mix the adhesive polymer or polymers and any formulation aids such as fillers, tableting excipients, lubricants, flavors, dyes, and the like and then compress the mixture.

The drug-containing or active layer 14 is first prepared by intimately admixing the drug with a permeation enhancer and any other formulation aids such as tableting excipients, dyes, flavors, taste-masking agents, stabilizers, enyzme inhibitors, lubricants, and the like. This can be formulated as a dry mix or accomplished by conventional wet granulation and screening techniques followed by drying. In either event, the blended drug-containing layer ingredients are then placed on top of the partially compressed adhesive layer and both layers are then compressed A person of ordinary skill in the art will recognize that the instant tablet can also be manufactured by making the drug-containing layer first and then the adhesive layer.

The compositions of the present invention will preferably be sized to provide between about 0.05 cm$^2$ and 10 cm$^2$ of surface area for contact between the drug-containing layer and the mucosa. Areas of between about 0.07 cm$^2$ and about 5 cm$^2$ are preferred with areas of between about 0.18 cm$^2$ and 5 cm$^2$ being optimal. The drug-containing or active layer will generally have a thickness of between about 0.1 and 3 mm with thicknesses of between about 0.5 and 2 mm being preferred.

The following examples are illustrative of methods of preparing bilayer tablets according to the present invention.

EXAMPLE 1

Bilayer tablets are prepared in the following manner. An adhesive layer was prepared by weighing 70 parts by weight polyethylene oxide (Polyox 301N; Union Carbide), 20 parts by weight polyacrylic acid (Carbopol 934P; B.F. Goodrich), and 10 parts by weight of a compressible xylitol/carboxymethyl cellulose filler (Xylitab 200; Xyrofin). These ingredients were mixed by rolling in a jar for 3 minutes. The mixture was then transferred to an evaporating dish and quickly wet granulated with absolute ethanol to a semi-dough-like consistency. This mass was immediately and rapidly forced through a 14 mesh (1.4 mm opening) stainless steel screen, to which the wet granules adhered. The screen was covered with perforated aluminum foil, and the wet granules were dried overnight at 30° C. The dried granules were removed from the screen and then passed through a 20 mesh (0.85 mm opening) screen to further reduce the size of the granules. Particles that did not pass through the 20 mesh screen were ground briefly with a mortar and pestle to minimize the amount of fines and then passed through the 20 mesh screen. The resulting granules were then placed in a mixing jar, and 0.25 parts by weight stearic acid and 0.06 parts by weight mint flavor (Universal Flavors) were added and blended to the granules. The final percentages by weight of the ingredients were thus 69.78% polyethylene oxide, 9.97% compressible xylitol/carboxymethyl cellulose filler, 19.94% polyacrylic acid, 0.25% stearic acid, and 0.06% mint flavor. A 50 mg amount of this mixture was placed on a 0.375 inch diameter die and precompressed on a Carver Press Model C with 0.25 metric ton pressure for a 3 second dwell time to form the adhesive layer.

The active layer was prepared by weighing 49.39 parts by weight of mannitol, 34.33 parts by weight of hydroxypropyl cellulose (Klucel L. F.; Aqualon, Wilmington, Del.) and 15.00 parts by weight of sodium taurocholate (Aldrich, Milwaukee, Wis.), and mixing by rolling in a jar for 3 minutes. The mixture was then transferred to an evaporating dish and quickly wet granulated with absolute ethanol to a semi-dough-like consistency. This mass was immediately and rapidly forced through a 14 mesh stainless steel screen, to which the wet granules adhered The screen was covered with perforated aluminum foil, and the granules were dried at 30° C. The dried granulation was then passed sequentially through 20 and 60 (0.25 mm opening) mesh screens to reduce particle size further Particles that did not pass through a screen were briefly ground with a mortar and pestle to minimize fines and then passed through the screen. The screened particles were weighed, and then 0.91 parts by weight of GLP-1(7–36)amide and 0.06 parts by weight of FD&C yellow #6HT aluminum lake dye were sequentially blended with the dry granulation by geometric dilution. The dyed granulation was then placed in a mixing jar and blended with 0.25 parts by weight magnesium stearate (lubricant) and 0.06 parts by weight mint flavor by rolling for 3 minutes. A 50 mg sample of this material was placed on top of the partially compressed adhesive layer and both layers were then compressed at 1.0 ton pressure for a 3 second dwell time to yield a bilayer tablet suitable for buccal delivery.

This procedure results in a gingival tablet wherein the active layer contains 0.91% by weight of GLP-1(7–36) amide, 15% by weight of NaTC, and 84.09% by weight of filler, lubricant, colorant, formulation aids, or flavoring agents.

EXAMPLE 2

The procedure of Example 1 was followed with the exception that the amounts of the components of the active layer were varied to provide an active layer containing 65.30% by weight mannitol, 34.33% hydroxypropyl cellulose, 0.25% magnesium stearate, 0.06% FD&C yellow #6HT aluminum lake dye, and 0.06% mint flavor. This procedure results in placebo tablets for use in double-blind in vivo studies with human volunteers.

EXAMPLE 3

The procedure of Example 1 was followed to prepare a buccal tablet wherein the active layer contained the same content but was prepared by dry blending and not by wet granulation.

EXAMPLE 4

This example describes a double-blind, placebo-controlled, crossover comparison with random assignment to treatment sequence. Eight healthy volunteers were selected for this in vivo study of blood glucose, insulin, glucagon, and GLP-1(7–36)amide levels in response to receiving either a drug-containing bilayer tablet containing 400 μg of GLP-1(7–36)amide or a placebo prepared according to Examples 1 and 2, respectively. Inclusion criteria for the volunteers were normal glucose tolerance, weight within 22<BMI<26, informed consent to participate in the study, and age between 20 and 60 years. Exclusion criteria were impaired glucose tolerance (2-hour glucose tolerance test; OGTT), gastrointestinal symptoms, ongoing medication or illness, acute infection, abnormal laboratory variables (hemoglobin, hematocrit, leucocytes, creatinine, bilirubin, calcium, potassium, sodium, alkaline phosphatase, gamma-GT, SGOT, SGPT, cholesterol, and triglycerides), and blood pressure greater than 185 mmHg systolic and/or 90 mmHg diastolic.

Subject numbers were allotted to the subjects in the order in which they were enrolled in the study. The number allotted to each subject determined the treatment sequence received. Subjects receiving treatment sequence 1 were treated with drug followed by placebo, and subjects receiving treatment sequence 2 were treated with placebo followed by drug.

Subjects were instructed to fast the night before a treatment. At the clinic, the subjects were given either a drug-containing bilayer tablet or placebo. At time 0 the bilayer tablet was applied to the gingiva with the active layer in contact with the tissue of the lip or inside of the cheek, and the subjects were placed in a rest position. The bilayer tablet was removed after 4.5 hours. No meals were allowed until a standard meal was given after 4.5 hours, and snacks were not permitted at any time. The standard meal contained 550 kcal, with 28%, 22%, and 50% of the energy from protein, fat, and carbohydrate, respectively. The test continued until 8 hours after application of the bilayer tablet, and the subjects left the hospital after 9 hours. The subjects were given their medications in the clinic by a nurse and were under observation at all times. Any symptoms or sensations disturbing or impairing the subjects' wellbeing during the experiments was carefully documented. Standard safety variables were determined under fasting conditions before each experiment. Blood glucose was monitored frequently and glucose infusion was available in case of hypoglycemia (<2.5 mmol/L). If any subject were to experience hypoglycemic symptoms, an extra blood glucose determination would be taken for safety reasons A washout period of 1–4 days was allowed between each experiment The study was completed within 6 weeks after enrollment of the first volunteer.

Blood samples were taken for pharmacokinetic analysis 10 minutes before application of the drug, and at 5, 10, 15, 20, 25, 30, 40, 50 60, 75, 90, 120, 150, 180, 210, 240, and 270 minutes and 6 and 8 hours after application of the drug. Samples were frozen until assayed for GLP-1(7–36)amide content by double antibody radioimmunoassay (RIA). The peptide content of bilayer tablet samples was also analyzed by HPLC. Average blood glucose, insulin, glucagon, and GLP-1(7–36)amide concentrations were calculated by area under the curve (AUC) using the trapezoidal rule. The maximal concentration ($C_{max}$), half-life ($T_{1/2}$), and time to maximal blood level ($T_{max}$) were calculated for GLP-1 (7–36)amide based on plasma levels of the peptide. Results were tested for normal distribution. A two-tailed t-test was carried out for normally distributed samples, and a Wilcoxon rank-sum test was used for data that were not normally distributed. All statistical tests used a level of significance of 0.05.

Figure 2:
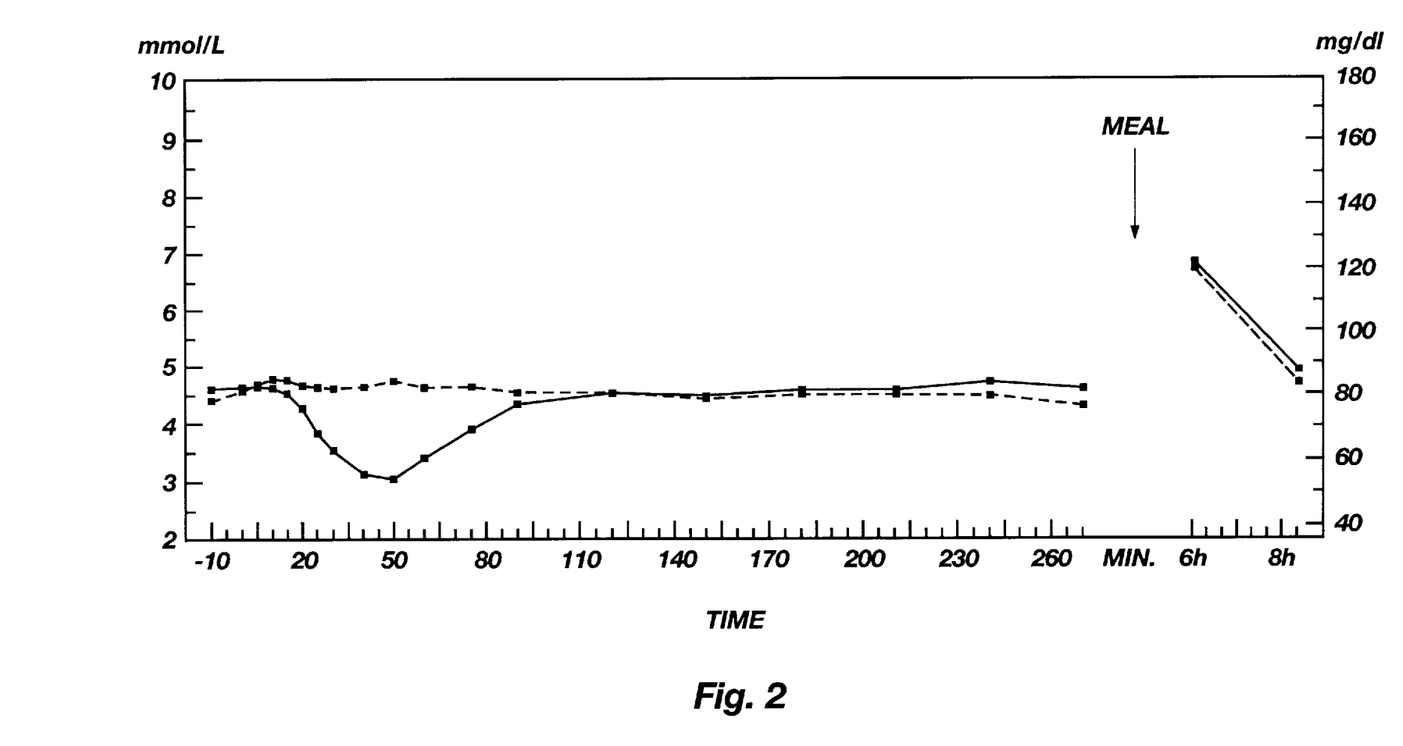
FIG. 2 shows the results of blood glucose determinations for fasting subjects given a placebo (dotted line) or GLP-1 (7–36)amide (solid line) by buccal administration of a bilayer tablet according to the present invention.

FIG. 2 shows the results of blood glucose determinations for subjects given the placebo (dotted line) or drug (solid line). For the placebo group, blood glucose levels remain relatively constant from 10 minutes before application of the bilayer tablet through 270 minutes after application thereof. Over the same time period, the blood glucose levels of subjects receiving GLP-1(7–36)amide drop below that of the placebo group by 20 minutes after application of the drug, reach a lowest level of about 3 mmol/L at about 50 minutes, and return to a normal level by about 90 minutes. Blood glucose levels of the two groups are indistinguishable after the meal. These data show that buccal administration of GLP-1(7–36)amide with the bilayer tablet according to the present invention results in significantly reduced blood glucose levels as compared to placebo controls.

Figure 3:
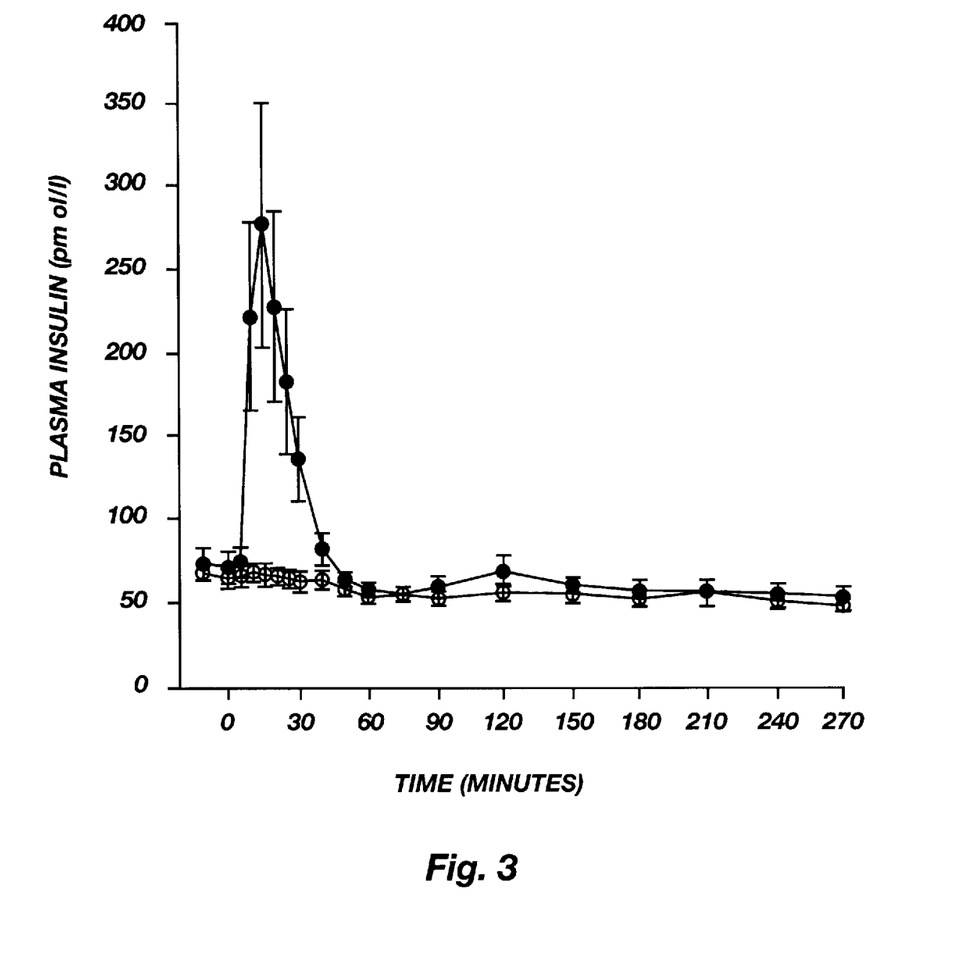
FIG. 3 shows the results of plasma insulin determinations for subjects given a placebo (○) or GLP-1(7–36)amide (●) by buccal administration of a bilayer tablet according to the present invention.

FIG. 3 shows the results of plasma insulin determinations for subjects given the placebo (○) or the drug (●). For the placebo group, the plasma insulin levels remain relatively constant or decline slightly over the course of 10 minutes prior to administration of the bilayer tablet to 270 minutes after administration thereof. For the group receiving GLP-1, the plasma insulin level rises sharply from a normal level at 10 minutes after administration of the drug to a level about three time normal at 15 minutes after administration. A peak plasma insulin level is reached about 20 minutes after administration of GLP-1(7–36)amide, and the level rapidly declines to normal by about 50 minutes. Otherwise, the insulin levels of the drug group track the insulin levels of the placebo group. Thus, buccal administration of GLP-1(7–36) amide results in a rapid increase of plasma insulin concentration followed by a rapid decrease, both within an hour of administration of the drug.

Figure 4:
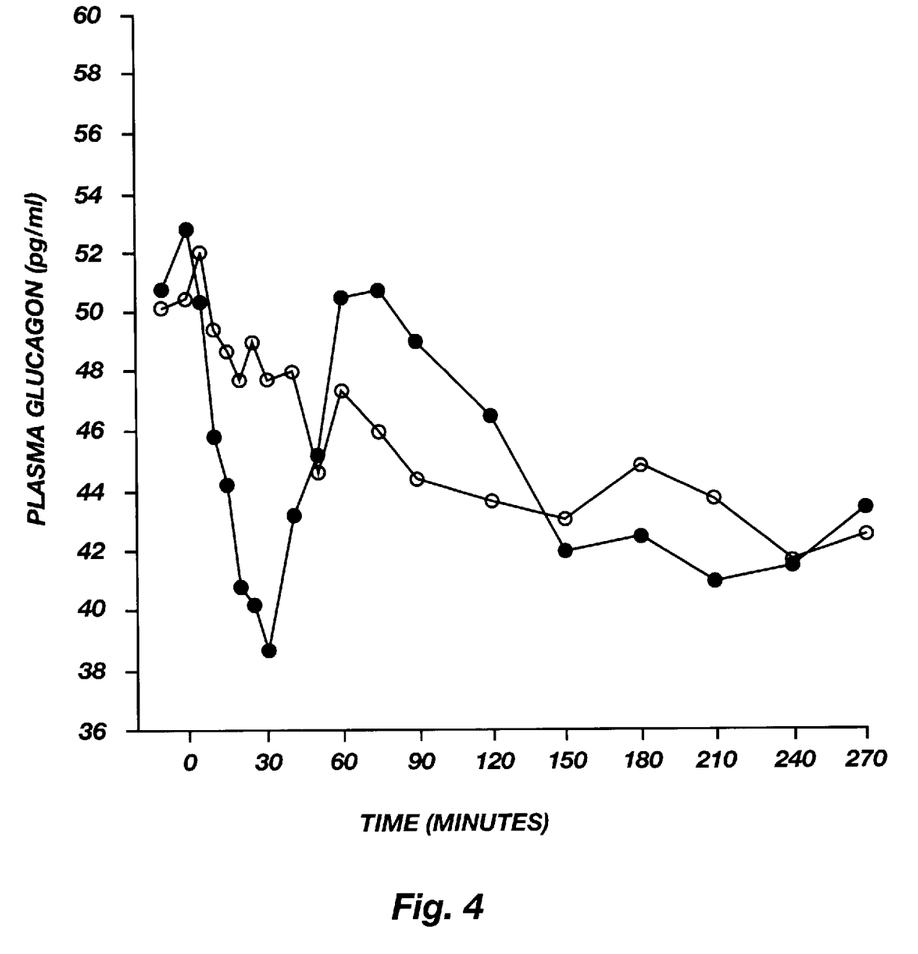
FIG. 4 shows the results of plasma glucagon determinations for subjects given a placebo (○) or GLP-1(7–36)amide (●) by buccal administration of a bilayer tablet according to the present invention.

FIG. 4 shows the results of plasma glucagon determinations for subjects given the placebo (○) or the drug (●). For the placebo group, the plasma glucagon level declines slowly and steadily from 10 minutes prior to administration of the bilayer tablet until 270 minutes after administration thereof. For the drug group, the plasma glucagon level declines sharply from time 0 until a level significantly lower than the placebo group is reached about 30 minutes later, and then the level rises sharply to a level significantly higher than the placebo group, reaching a peak about 60–75 minutes after administration. From this peak, the plasma glucagon level declines steadily until it tracks the level of the placebo group beginning at about 150 minutes after administration of the drug. These data show that buccal administration of GLP-1(7–36)amide quickly lowers plasma glucagon levels below those of the placebo group and then raises them to higher than normal levels before they reach normal levels again about 150 minutes after administration.

Figure 5:
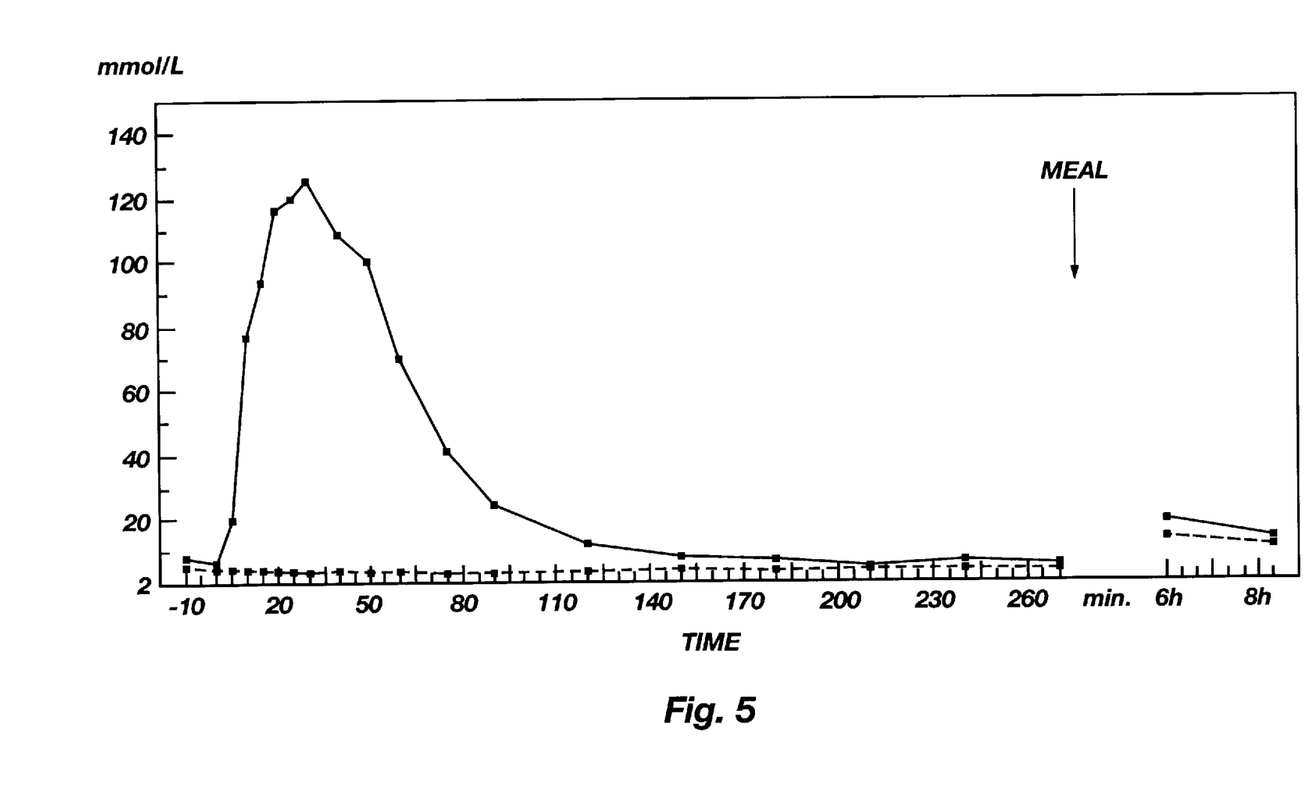
FIG. 5 shows the results of plasma GLP-1(7–36)amide determinations for subjects given a placebo (dotted line) or the drug (solid line) by buccal administration of a bilayer tablet according to the present invention.

FIG. 5 shows the results of plasma GLP-1(7–36)amide determinations for subjects given the placebo (dotted line) or drug (solid line). For the placebo group, the amount of GLP-1(7–36)amide in the plasma remains fairly constant at a very low level from 10 minutes prior to administration of the drug until 270 minutes after administration thereof. After the meal, the plasma GLP-1(7–36)amide level rises and then declines steadily over time. For the drug group, the plasma GLP-1(7–36)amide level rises sharply beginning within 5 minutes of administration and reaches a peak about 30 minutes after administration. The GLP-1(7–36)amide level then declines rapidly until about 90 minutes after administration, and then declines more slowly to a level that tracks that of the placebo group beginning at about 150 minutes After the meal, the GLP-1(7–36)amide level is approximately the same as that of the placebo group. These results show that buccal administration of GLP-1(7–36) amide results in rapid absorption through the buccal mucosa into the bloodstream and that elevated levels of GLP-1 (7–36)amide remain in the blood until about 150 minutes after administration.

Taken together, these data show that buccal administration of GLP-1(7–36)amide with the bilayer tablet of the instant invention results in rapid absorption into the bloodstream that leads to a sharp rise in the amount of plasma insulin and a corresponding decrease in the amount of glucose in the blood. Further, the blood glucose level does not result in hypoglycemia.

EXAMPLE 5

In this example, the relative bioavailability of GLP-1 (7–36)amide by buccal administration is compared to that of subcutaneously administered GLP-1. This was done in comparison to published data. Two studies providing intravenous infusion data in fasting individuals are available: D. M. Nathan et al., Insulinotropic Action of Glucagonlike peptide-1-(7–37) in Diabetic and Nondiabetic Subjects, 15 *Diabetes Care* 270 (1992); C. ørskov et al., Biological Effects and Metabolic Rates of Glucagonlike Peptide-1 7–36 amide and Glucagonlike Peptide-1 7–37 in Healthy Subjects is Indistinguishable, 42 *Diabetes* 658 (1993). Both of these studies support an approximate clearance of 15 ml/min/kg.

Figure 6:
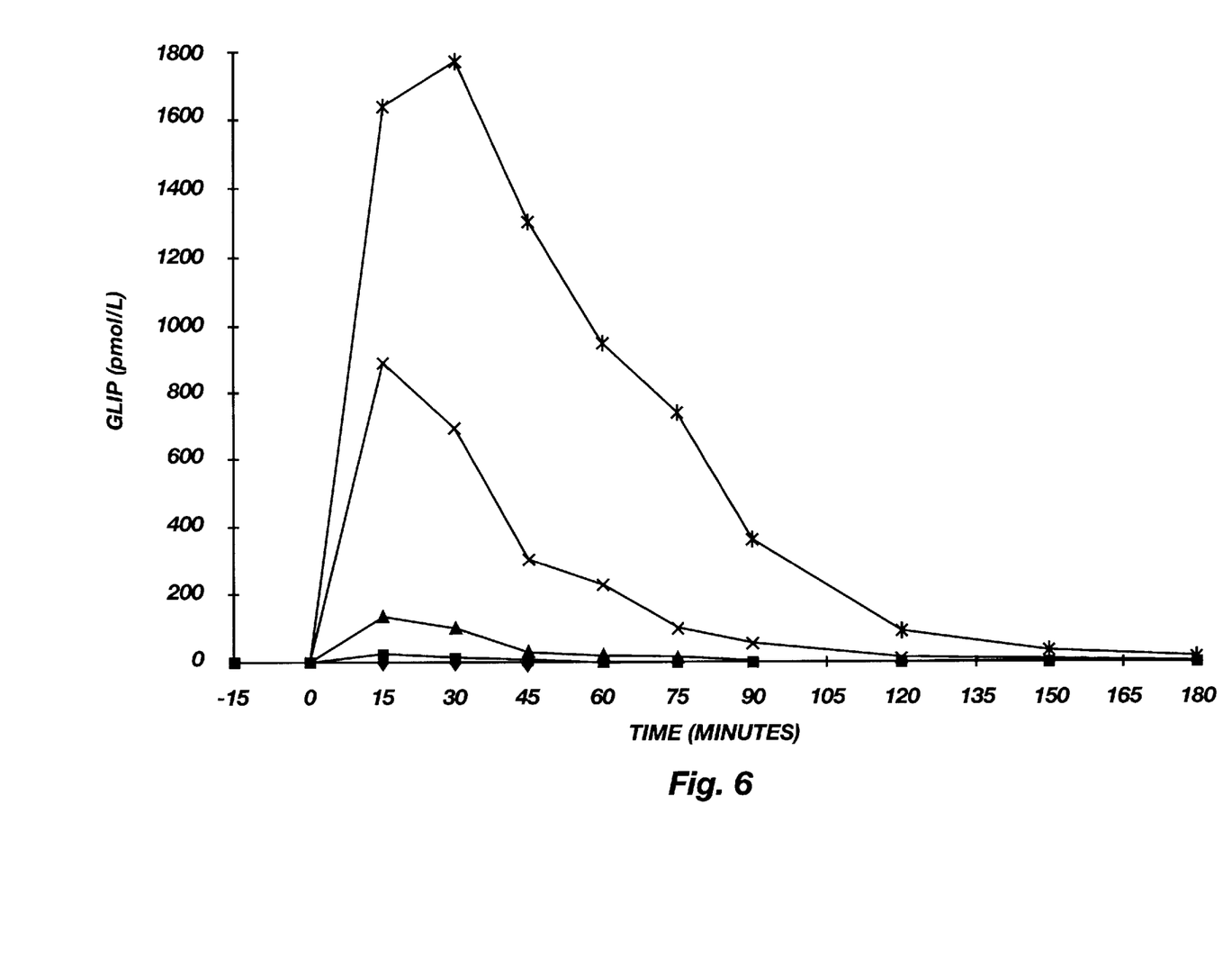
FIG. 6 shows the results of plasma GLP-1 determinations for fasting subjects given the drug by subcutaneous administration at various doses: (♦) placebo; (■) 0.15 nmol/kg; (▲) 0.50 nmol/kg; (X) 1.50 nmol/kg; (☆) 4.50 nmol/kg.

A study by M. A. Nauck of subcutaneous administration of GLP-1 to fasting subjects illustrates changes in the pharmocokinetics with dose (FIG. 6). This could be due to changes in bioavailability with dose, changes in clearance with dose, or a combination of both effects. At any rate, regression analysis of all the results indicate a clearance of about 40 ml/min/kg, which is consistent with a bioavailability of 38% by subcutaneous administration relative to intravenous administration.

The data summarized in FIG. 5 were analyzed by AUC to provide an estimate of relative bioavailability by buccal administration as compared to subcutaneous administration. These data are shown in Table 1.

TABLE 1

GLP-1(7-36)amide Pharmacokinetic Summary - Buccal Delivery

| Subject | Dose (nmol) | AUC (pmol-min/L) | Dose (nmol) | Bioavail-ability (%) | Half-Life (30–210 min) |
|---|---|---|---|---|---|
| 901 | 119 | 9113 | 9.57 | 8.04 | 27.13 |
| 902 | 119 | 7250 | 7.61 | 6.40 | 23.99 |
| 903 | 119 | 8753 | 9.19 | 7.72 | 29.49 |
| 904 | 119 | — | — | — | — |
| 905 | 119 | 8410 | 8.83 | 7.42 | 18.80 |
| 906 | 119 | 11343 | 11.91 | 10.01 | 24.38 |
| 907 | 119 | 3278 | 3.44 | 2.89 | 29.95 |
| 908 | 119 | — | — | — | — |
| Mean | 119 | 8024 | 8.43 | 7.08 | 25.62 |
| SD |  | 2683 | 2.82 | 2.37 | 4.17 |

These data show a relative bioavailability of 27% as compared to the data of FIG. 6.

EXAMPLE 6

Bilayer tablets were prepared essentially as in Example 1 except the active layer was prepared by dry blending 206 mg of hydroxypropyl cellulose (Klucel E. F.; Aqualon), 241.4 mg mannitol, 90 mg NaTC, and 60 mg human insulin. To this blend was added 800 $\mu$l of absolute ethanol, and the mixture was wet blended to give a wet granulation having a dough-like consistency. The wet granulation was passed through a 14 mesh screen and allowed to dry overnight in a draft oven at 25° C. The dried pre-granulation was passed through a 20 mesh sieve and then placed in a glass vial with 1.5 mg of magnesium stearate, 0.36 mg mint flavor, and 0.72 mg of Colorcon FD&C yellow #6HT aluminum lake dye and dry blended again. A 50 mg amount of this material was placed on top of the partially compressed adhesive layer and both layers were then compressed at 1 ton pressure for a dwell time of 3 seconds to yield a bilayer tablet suitable for buccal delivery. This bilayer tablet has an active layer surface area of about 0.71 $cm^2$, wherein the active layer contains 140 U (5 mg) human insulin (10% by weight), 7.5 mg NaTC (15% by weight), 17.7 mg hydroxypropyl cellulose (34.33% by weight), 20.1 mg mannitol (40.24% by weight), 0.25% by weight magnesium stearate, 0.06% mint flavor, and 0.12% by weight FD&C yellow #6HT aluminum lake dye.

EXAMPLE 7

The procedure of Example 6 was followed except the drug-containing layer contained 20% by weight of human insulin and 30.24% by weight of mannitol.

EXAMPLE 8

The procedure of Example 6 was followed except the drug-containing layer contained 48.24% by weight mannitol and 2.0% by weight amylin, and the bilayer tablet was fabricated with a 0.25 inch diameter having a 25 mg active layer.

EXAMPLE 9

The procedure of Example 8 was followed except the final concentrations of amylin and mannitol in the active layer were 4.0% by weight and 46.24% by weight, respectively.

EXAMPLE 10

The procedure of Example 6 was followed with the exception that the drug-containing layer contained 49.44% by weight mannitol and 0.80% by weight desmopressin.

EXAMPLE 11

The procedure of Example 6 was followed except that the active layer contained 42.24% by weight mannitol and 8.0% by weight parathyroid hormone.

EXAMPLE 12

The procedure of Example 6 was followed except the active layer contained 45.24% by weight mannitol and 5.0% insulin B fragment.

EXAMPLE 13

The procedure of Example 6 was followed with the following exceptions. In the active layer, human insulin was replaced by 2% by weight of a proprietary peptide drug (hereinafter, "peptide X") having a molecular weight of 3500–4000, yellow dye was omitted, and the percent by weight of mannitol was increased to 48.36%. In the adhesive layer, 0.015% by weight of FD&C blue #1 aluminum lake dye was added, and the percents by weight of polyethylene oxide (69.7725%), polyacrylic acid (19.935%), and compressible xylitol/carboxymethyl cellulose (9.9675%) were adjusted. The adhesive layer comprised 80 mg of dry granulation precompressed with 0.75 ton pressure for 3 seconds; and the active layer comprised 100 mg compressed with 0.25 ton pressure for 3 seconds.

EXAMPLE 14

The procedure of Example 13 was followed with the exception that the amount of peptide X was 1% by weight and the amount of mannitol was 49.35% by weight.

EXAMPLE 15

The procedure of Example 14 was followed with the exception that 10% by weight of ammonium glycirrhizinate (MAGNASWEET 100; MacAndrews & Forbes Company, Camden, N.J.) was added to the active layer, and the amount of mannitol was correspondingly reduced.

EXAMPLE 16

Transbuccal transport of peptide X was demonstrated using the dog buccal mucosa model. The dog was selected as the animal model because the structure of dog buccal tissue is histologically similar to that of human tissue C. Ebert et al., Transbuccal Absorption of Diclofenac Sodium in a Dog Animal Model, in Controlled-Release Technology 310–21 (P. Lee, W. Good, eds., ACS Symposium Series, No. 348, American Chemical Society, Washington, D.C., 1987). Rodents tend to have keratinized buccal tissue while dogs, like humans, show well vascularized buccal tissue with no keratinized layer.

Bilayer tablets prepared according to Examples 13–15 were tested in in vivo experiments to determine their effectiveness in delivering peptide X systemically to dogs. Mongrel dogs each weighing 30–35 kg were conditioned for one month prior to use. The dogs were mildly sedated with acepromazine, but were awake for the duration of each experiment. Tablets were attached to the gingiva with the active layer contacting and in drug transfer relationship to the buccal mucosa of the upper lip. Nylon muzzles were used to prevent the animals from licking the tablets. In this model, normal salivary functions were preserved and no irrigation was required. The saphenous vein was catheterized to permit venous blood sampling. Blood samples were collected into citrate "VACUTAINER" tubes and immediately chilled on ice for 15 minutes and then centrifuged for 10 minutes at 3400 rpm. The resultant supernatant plasma was then collected and stored in capped polypropylene tubes at −70° C. until analyzed for peptide X content.

The results of these transmucosal delivery experiments of peptide X are summarized in Table 2.

TABLE 2

Peptide X - Buccal Delivery

| Tablets Administered | | | | Results | | |
|---|---|---|---|---|---|---|
| | | | mg | | Peptide absorbed | |
| Type | No. | $cm^{2a}$ | peptide | % $F_{sc}^{b}$ | mg | $mg/cm^2$ |
| EX. 7 | 1 | 0.71 | 1.64 | 8.29 ± 2.52 | 0.0325 | 0.0456 |
| EX. 8 | 2 | 1.43 | 1.64 | 10.17 ± 9.68 | 0.0460 | 0.0323 |
| Ex. 9 | 2 | 1.43 | 1.64 | 7.75 ± 1.57 | 0.0281 | 0.0197 |

Figure 7:
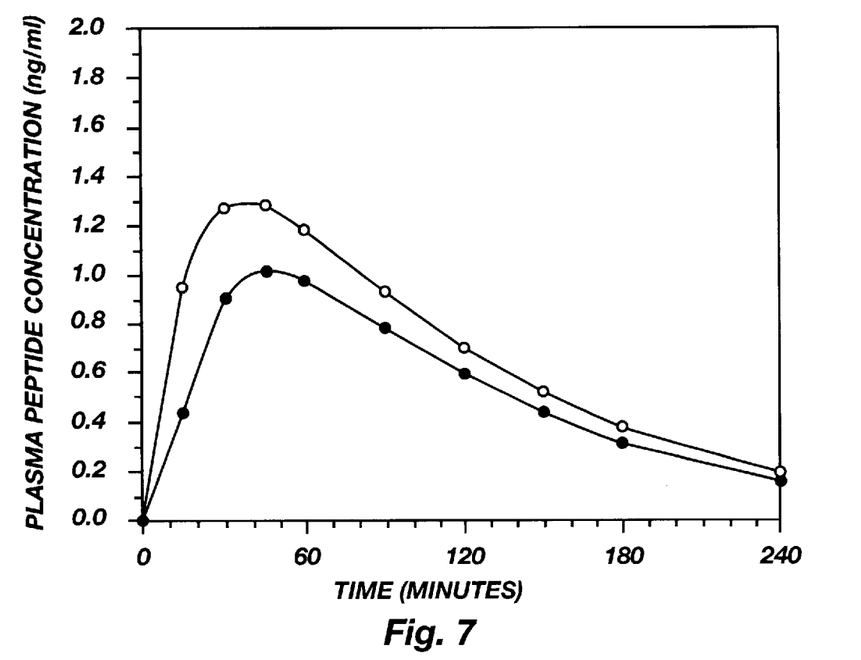
FIG. 7 shows plasma concentration profiles for buccally delivered (○) and subcutaneously injected (●) peptide X.

[a]Nominal surface area.
[b]Apparent Bioavailability = % $F_{sc}$ = $Dose_{sc}$ $(AUC_{0 \to \infty})_{BUC}$ ÷ $Dose_{BUC}$ $(AUC_{0 \to \infty})_{SC}$ These results show that peptide X is delivered to the bloodstream by transmucosal delivery with the bilayer tablet dosage forms of the present invention. The apparent bioavailability of peptide X averaged about 8.74% as compared to subcutaneous injection. Times to maximum blood levels were in the range of about 30 to 60 minutes, averaging about 40 minutes for a one-tablet application and about 50 minutes for two-tablet applications. Experiments with formulations containing ammonium glycirrhizinate appeared to give longer time to maximum concentration, ranging from about 60–100 minutes and averaging about 85 minutes. Maximal blood concentrations ($C_{max}$) averaged about 1.5 ng/ml for 1% drug loadings in 2 tablets and about 1.3 ng/ml for 2% drug loadings in 1 tablet. FIG. 7 shows that the profiles of plasma peptide concentrations of peptide X by buccal delivery (○; 1.64 mg peptide) and subcutaneous injection (●; 0.1 mg peptide) are very similar.

EXAMPLE 17

The procedure of Example 16 was followed with the exception that salmon calcitonin was substituted for peptide X, and tablet sizes and numbers were varied in some experiments. The results are summarized in Table 3.

TABLE 3

Salmon Calcitonin - Buccal Delivery

| Dog ID# | No. Tabs | $cm^2$ | $AUC_\infty$ buc/iv | ng Absorbed |
|---|---|---|---|---|
| 3-31 | 2 | 1.27 | 139/76 | 72,958 |
| 3-144 | 2 | 1.27 | 66/159 | 16,461 |
| 3-144 | 2 | 1.27 | 84/159 | 20,989 |
| 3-144 | 2 | 0.71 | 26/159 | 6,535 |
| 3-293 | 2 | 0.71 | 64/106 | 23,379 |
| 4-99 | 2 | 1.27 | 38/87 | 17,614 |

These results show that salmon calcitonin is delivered into the bloodstream of a warm-blooded animal by buccal delivery via a bilayer tablet according to the present invention.

EXAMPLE 18

Figure 8:
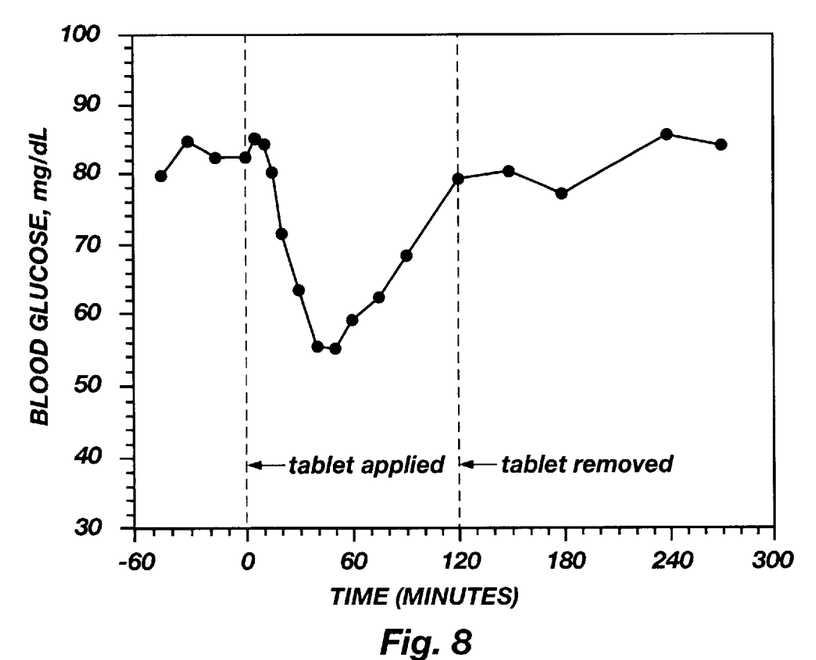
FIG. 8 shows average blood glucose levels of 4 dogs given insulin by buccal administration of a bilayer tablet according to the present invention.

The procedure of Example 16 was followed with insulin-containing tablets prepared according to Example 6. The results shown in FIG. 8 are the average of 4 dogs, each given one 0.375 inch diameter buccal tablet containing 5 U/kg of drug. These results show that blood glucose levels drop sharply beginning about 15 minutes after application of the tablet and reach a low level about 40 minutes after application of the tablet. Beginning about 60 minutes after application, the blood glucose levels start to rise again, reaching normal levels about 120 minutes after application. These results show that buccal delivery of insulin is effective in controlling blood glucose levels.

We claim:

1. A system for transmucosally administering a drug to the oral cavity comprising an adhesive layer comprising a hydrophilic polymer having one surface adapted to contact a first tissue of the oral cavity and adhere thereto when wet and an opposing surface in contact with and adhering to an adjacent drug-containing layer comprising an effective amount of a drug and optionally an effective amount of a permeation enhancer, said drug-containing layer adapted to contact and be in drug transfer relationship with a mucosal tissue of the oral cavity when said adhesive layer contacts and adheres to said first tissue.

2. The system of claim 1 wherein said permeation enhancer is a member selected from the group consisting of cell envelope disordering compounds, solvents, steroidal detergents, chelators, surfactants, non-surfactants, fatty acids, and mixtures thereof.

3. The system of claim 2 wherein said permeation enhancer is a steroidal detergent.

4. The system of claim 3 wherein said permeation enhancer is a bile salt.

5. The system of claim 4 wherein said drug is a peptide.

6. The system of claim 5 wherein said hydrophilic polymer comprises at least one member selected from the group consisting of hydroxypropyl cellulose, hydroxypropyl methylcellulose, hydroxyethylcellulose, ethylcellulose, carboxymethyl cellulose, dextran, gaur-gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and mixtures thereof.

7. The system of claim 6 in the form of a bilayer tablet wherein said adhesive layer additionally contains one or more members selected from the group consisting of fillers, tableting excipients, lubricants, flavors; and dyes and wherein said drug-containing layer additionally contains one or more members selected from the group consisting of tableting excipients, fillers, flavors, taste-masking agents, dyes, stabilizers, enyzme inhibitors, and lubricants.

8. The system of claim 7 wherein said bile salt enhancer is a salt of a conjugate of a bile acid with taurine.

9. The system of claim 8 wherein said hydrophilic polymer comprises a mixture of polyethylene oxide and polyacrylic acid.

10. The system of claim 9 wherein said peptide is a member selected from the group consisting of insulinotropic peptides and precursors, analogues, and fragments thereof.

11. The system of claim 10 wherein said peptide is a member selected from the group consisting of GLP-1(7–36) amide, and precursors, analogues, and fragments thereof.

12. The system of claim 11 wherein said peptide is GLP-1(7–36)amide.

13. The system of claim 10 wherein said peptide is a member selected from the group consisting of insulin and precursors, analogues, and fragments thereof.

14. The system of claim 13 wherein said peptide is insulin.

15. The system of claim 10 wherein said peptide is member selected from the group consisting of amylin and precursors, analogues, and fragments thereof.

16. The system of claim 9 wherein said peptide is a member selected from the group consisting of calcitonin and precursors, analogues, and fragments thereof.

17. The system of claim 16 wherein said peptide is calcitonin.

18. The system of claim 9 wherein said peptide is a member selected from the group consisting of desmopressin and precursors, analogues, and fragments thereof.

19. The system of claim 18 wherein said peptide is desmopressin.

20. The system of claim 9 wherein said peptide is a member of the group consisting of parathyroid hormone and precursors, analogues, and fragments thereof.

21. The system of claim 20 wherein said peptide is parathyroid hormone.

22. The system of claim 1 wherein said first tissue is gingival tissue and said mucosal tissue is buccal mucosa.

23. A method for transmucosally administering a drug to an oral cavity comprising applying to a first tissue of the oral cavity a system comprising an adhesive layer comprising a hydrophilic polymer having one surface adapted to contact said first tissue of the oral cavity and adhere thereto when wet and an opposing surface in contact with and adhering to an adjacent drug-containing layer comprising an effective amount of a drug and optionally an effective amount of a permeation enhancer, said drug-containing layer adapted to contact and be in drug transfer relationship with a mucosal tissue of the oral cavity when said adhesive layer contacts and adheres to said first tissue.

24. The method of claim 23 wherein said permeation enhancer is a member selected from the group consisting of cell envelope disordering compounds, solvents, steroidal detergents, chelators, surfactants, non-surfactants, fatty acids, and mixtures thereof.

25. The method of claim 24 wherein said permeation enhancer is a steroidal detergent.

26. The method of claim 25 wherein said permeation enhancer is a bile salt.

27. The method of claim 26 wherein said drug is a peptide.

28. The method of claim 27 wherein said hydrophilic polymer comprises at least one member selected from the group consisting of hydroxypropyl cellulose, hydroxypropyl methylcellulose, hydroxyethylcellulose, ethylcellulose, carboxymethyl cellulose, dextran, gaur-gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and mixtures thereof.

29. The method of claim 28 in the form of a bilayer tablet wherein said adhesive layer additionally contains one or more members selected from the group consisting of fillers, tableting excipients, lubricants, flavors, and dyes and wherein said drug-containing layer additionally contains one or more members selected from the group consisting of tableting excipients, fillers, flavors, taste-masking agents, dyes, stabilizers, enyzme inhibitors, and lubricants.

30. The method of claim 29 wherein said bile salt enhancer is a salt of a conjugate of a bile acid with taurine.

31. The method of claim 30 wherein said hydrophilic polymer comprises a mixture of polyethylene oxide and polyacrylic acid.

32. The method of claim 31 wherein said peptide is a member selected from the group consisting of insulinotropic peptides and precursors, analogues, and fragments thereof.

33. The method of claim 32 wherein said peptide is a member selected from the group consisting of GLP-1(7–36) amide, and precursors, analogues, and fragments thereof.

34. The method of claim 33 wherein said peptide is GLP-1(7–36)amide.

35. The method of claim 32 wherein said peptide is a member selected from the group consisting of insulin and precursors, analogues, and fragments thereof.

36. The method of claim 35 wherein said peptide is insulin.

37. The method of claim 32 wherein said peptide is member selected from the group consisting of amylin and precursors, analogues, and fragments thereof.

38. The method of claim 31 wherein said peptide is a member selected from the group consisting of calcitonin and precursors, analogues, and fragments thereof.

39. The method of claim 38 wherein said peptide is calcitonin.

40. The method of claim 31 wherein said peptide is a member selected from the group consisting of desmopressin and precursors, analogues, and fragments thereof.

41. The method of claim 40 wherein said peptide is desmopressin.

42. The method of claim 31 wherein said peptide is a member of the group consisting of parathyroid hormone and precursors, analogues, and fragments thereof.

43. The method of claim 42 wherein said peptide is parathyroid hormone.

44. The method of claim 23 wherein said first tissue is gingival tissue and said mucosal tissue is buccal mucosa.

* * * * *